United States Patent
Bourgeois et al.

(10) Patent No.: US 8,067,644 B2
(45) Date of Patent: Nov. 29, 2011

(54) PROCESS FOR CONDUCTING AN ORGANIC REACTION IN IONIC LIQUIDS

(75) Inventors: Daniel Martin Bourgeois, Mason, OH (US); Gregory Scot Miracle, Hamilton, OH (US); Phillip John Porter, Mason, OH (US); Eva Boros, Sulzbach am Taunus (DE); Kenneth Richard Seddon, Donaghadee (GB); Harambage Quintus Nimal Gunaratne, Belfast (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/641,818

(22) Filed: Dec. 18, 2009

(65) Prior Publication Data

US 2011/0152566 A1      Jun. 23, 2011

(51) Int. Cl.
*C07C 45/61*   (2006.01)
*C07C 35/18*   (2006.01)
*C07C 69/75*   (2006.01)

(52) U.S. Cl. ........ 568/343; 568/349; 568/378; 568/826; 560/128

(58) Field of Classification Search .................. 568/343, 568/349, 378, 826
See application file for complete search history.

(56) References Cited

U.S. PATENT DOCUMENTS 4,334,098 A   6/1982   Mookherjee et al.
6,573,405 B1  6/2003   Abbott et al.

OTHER PUBLICATIONS

PCT International Search Report, date mailed Dec. 17, 2009, 16 pages.
Ayyar, et al., Synthesis of δ—Damascone [*trans*-1-(2,6,6-Trimethylclohex-3-enyl) but-2-en-1-one] and β-Damascenone [*trans*-1-(2,6,6-Trimethylcyclohexa-1,3-dienyl) but-2-en-1-one] *Journal of the Chemical Society Perkin Trans.*, 1975, 1, pp. 1727-1736.
Abbott, Andrew P., et al., "Quaternary ammonium zinc- or tin-containing ionic liquids: water insensitive, recyclable catalysts for Diels-Alder reactions," *Green Chemistry*, vol. 4, pp. 24-26, 2002.
Dyson, Paul J., et al., "Effect of Lewis acis on the Diels-Alder reaction in ionic liquids with different activation modes," *Journal of Physical Organic Chemistry*, vol. 21, pp. 264-270, 2008.
Kumar, Anil, et al., "Converting exo-Selective Diels-Alder Reaction to endo-Selective in Chloroaluminate Ionic Liquids," *The Journal of Organic Chemistry*, 2004, 4, pp. 1419-1420.
Lee, C. W.a, "Diels-Alder Reactions in Chloroaluminate Ionic Liquids: Acceleration and Selectivity Enhancement," Tetrahedron Letters, Elsevier, Amsterdam, vol. 40, pp. 2461-2464, 1999.
U.S. Appl. No. 12/641,786, filed Dec. 18, 2009, Daniel Martin Bourgeois, et al.

*Primary Examiner* — Sikarl Witherspoon
(74) *Attorney, Agent, or Firm* — Stephen T. Murphy

(57) ABSTRACT

The present disclosure describes processes for producing cyclohexenes using Lewis acidic ionic liquids comprising the steps of providing to a reactor an α,β-unsaturated carbonyl dienophile, providing to the reactor a 1,3-diene, providing a Lewis acidic ionic liquid to the reactor; and reacting the α,β-unsaturated carbonyl dienophile with 1,3-diene to form a substituted cyclohexene product. The α,β-unsaturated carbonyl dienophile can be mesityl oxide, the 1,3-diene can be piperylene; and the Lewis acidic ionic liquid can be $AlCl_3$:[$C_2$mim]Cl; $AlCl_3$:[$C_8$mim]Cl; or mixtures thereof.

21 Claims, 1 Drawing Sheet

Fig. 1

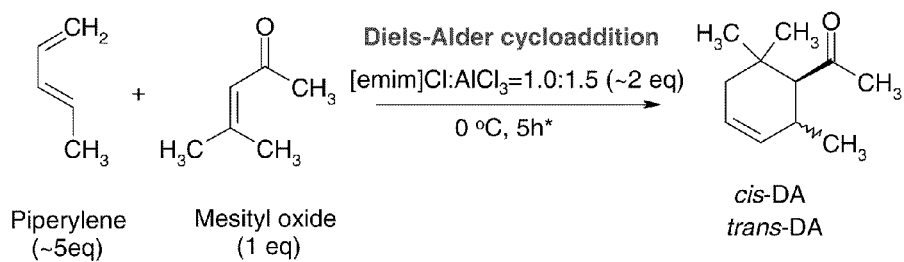

Piperylene (~5eq) + Mesityl oxide (1 eq) → Diels-Alder cycloaddition, [emim]Cl:AlCl$_3$=1.0:1.5 (~2 eq), 0 °C, 5h* → cis-DA, trans-DA

Fig. 2

| Mesityl oxide | Piperylene | Solvent / Catalyst | Product yield by NMR / % | |
|---|---|---|---|---|
| mmol/cm$^3$ | eq./mmol/cm$^3$ | Type | DCE Sample | DNB Sample |
| 10.0/1.14 | 5.0/50.0/4.93 | AlCl$_3$:[C$_2$mim]Cl=2:1 | 62.43 | 73.93 |
| 10.0/1.14 | 1.5/15.0/1.48 | AlCl$_3$:[C$_2$mim]Cl=2:1 | 0.00 | 0.00 |
| 10.0/1.14 | 5.0/50.0/4.93 | AlCl$_3$:[C$_2$mim]Cl=3:1 | 0.00 | 30.09 |
| 10.0/1.14 | 1.5/15.0/1.48 | AlCl$_3$:[C$_2$mim]Cl=3:1 | - | 7.05 |
| 10.0/1.14 | 5.0/50.0/4.93 | AlCl$_3$:[C$_8$mim]Cl=1.1:1 | 88.50 | 52.96 |
| 10.0/1.14 | 1.5/15.0/1.48 | AlCl$_3$:[C$_8$mim]Cl=1.1:1 | 0.00 | 8.73 |
| 10.0/1.14 | 5.0/50.0/4.93 | AlCl$_3$:[C$_8$mim]Cl=2:1 | - | 48.10 |
| 10.0/1.14 | 1.5/15.0/1.48 | AlCl$_3$:[C$_8$mim]Cl=2:1 | 0.00 | 3.45 |
| 10.0/1.14 | 5.0/50.0/4.93 | Al(OTf)$_3$:[C$_8$mim][OTf]=0.85:1 | 0.00 | 26.98 |
| 10.0/1.14 | 5.0/50.0/4.93 | Al(OTf)$_3$:[C$_8$mim][OTf]=2:1 | 31.29 | 22.27 |

PROCESS FOR CONDUCTING AN ORGANIC REACTION IN IONIC LIQUIDS

FIELD OF THE INVENTION

The present invention is related to processes for producing cyclic organic compounds using Lewis acidic ionic liquids. Specifically, substituted cyclohexenes may be synthesized in Diels-Alder type cycloadditions using Lewis acidic ionic liquids in the reaction medium. The cyclohexene products have use as components in commercial compositions.

BACKGROUND OF THE INVENTION

Perfume and aroma enhancing compounds are widely used as additives in the detergent and food industries. These compounds are used, for example, to augment or enhance the aromas of certain detergent compositions and perfumes, or to enhance the aroma and flavor characteristics of certain food or tobacco products among other products. Compounds with floral, fruity, woody, or other pleasing aroma are particularly desirable.

Many of these compounds have specific molecular features, such as the presence of a cyclic ring and/or a ketone, ester or other carbonyl derivative. For example, many fragrance components may include a substituted cyclohexene structure. These structures include, for example, various isomers of ionone, isomers of damascone, isomers of cyclogeranate, and isomers of irone. Other cyclic fragrance compounds are also known.

The damascones, including α-damascone, β-damascone, and δ-damascone are examples of compounds having pleasing floral, fruity aromas used in the perfumery art. The damascone isomers differ in the position of the ring double bond as shown in Scheme 1.

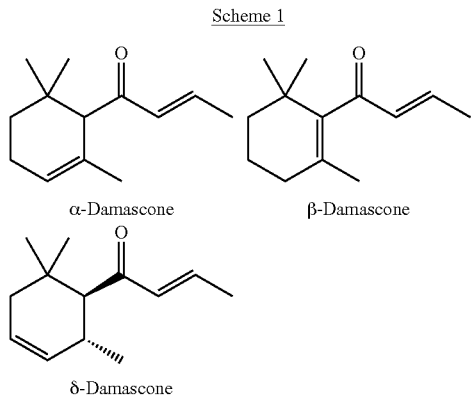

For example, trans,trans-δ-damascone is one of the most widely used fragrance additives in the detergent and food industries. Therefore, the industrial scale production of δ-damascone and other related compounds is of great interest.

Ayyer et al., *Journal of the Chemical Society Perkin Trans.*, 1975, 1, 1727-1736 discloses a 3-step synthesis of damascone starting from 1,3-pentadiene (piperylene) and mesityl oxide. The synthesis of the isomers of damascone involved three separate reaction processes, a Diels-Alder cycloaddition, epimerization of the resulting cyclohexenyl methyl ketone, and condensation/elimination with acetaldehyde in an aldol condensation process.

The Diels-Alder cycloaddition of piperylene as the diene and mesityl oxide as the dienophile forms a mixture of trans and cis-1-(2,6,6-trimethylcyclohex-3-en-1-yl)ethanone (Equation 1). Prior art references utilize the Ayyer method or slight modifications thereof. Ayyer disclosed a Lewis acid ($AlCl_3$) catalyzed Diels-Alder using conventional organic solvents ($CH_2Cl_2$), which affords the cyclohexene product in low yield (45%). Further optimization by other groups increased yields to 63% (U.S. Pat. No. 4,334,098 to Mookherjee et al.) using toluene as solvent. The cycloadduct is a mixture of the cis and trans ring isomers, with the cis-isomer of the cycloadduct predominating.

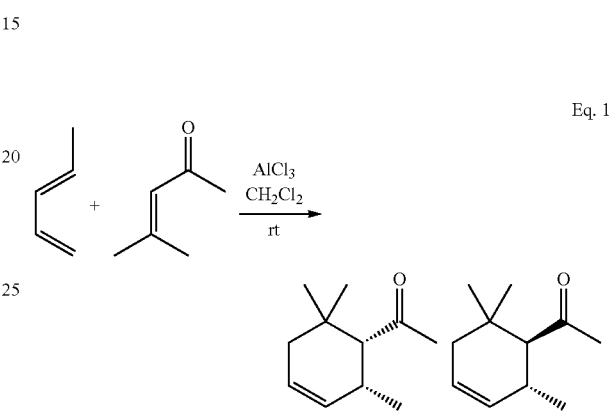

The prior art Lewis acid catalyzed Diels-Alder cycloadditions to form 1-(2,6,6-trimethylcyclohex-3-en-1-yl)ethanone suffer from low yields and result in a mixture of cis and trans ring isomers. Further, the reaction requires a large excess of piperylene and aluminum chloride ($AlCl_3$) and results in undesirable self polymerization of the piperylene diene. In addition, the use of aluminum chloride results in formation of aluminum hydroxide upon workup, resulting in handling and disposal problems of the aluminum hydroxide solid, particularly on an industrial scale. Isolation of the cycloadduct product also requires steam distillation, extraction, and fractional distillation to obtain a purified mixture of cis and trans-cyclohexene product. Finally, because of the high reaction dilutions, slow additions of reagents, large reaction vessels, long reaction times, and complex workup requirements, utilizing the conventional Diels-Alder cycloaddition technology on industrial scale is problematic.

Thus, for a commercially viable production of the isomers of damascone and other cyclohexane and cyclohexene based perfume components, rapid and efficient syntheses of cyclohexene intermediates, including for example, 1-(2,6,6-trimethylcyclohex-3-en-1-yl)ethanone, are necessary.

SUMMARY OF THE INVENTION

The present disclosure provides for the synthesis of substituted cyclohexene reaction products from acyclic materials in high yield and in a process suitable for scale-up to industrial scale.

According to one embodiment, the present disclosure provides for a process for producing substituted cyclohexenes. The process comprising the steps of providing to a reactor an α,β-unsaturated carbonyl dienophile of Formula I:

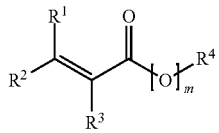

where $R^1$, $R^2$, $R^3$ and $R^4$ are each independently selected from the group consisting of H and $C_1$-$C_4$ alkyl or any of $R^1$ and $R^2$, $R^1$ and $R^4$, $R^3$ and $R^4$, or $R^2$ and $R^3$ may optionally be joined together to form a 5-, 6-, or 7-membered ring, and m is 0 or 1; providing to the reactor a 1,3-diene of Formula II

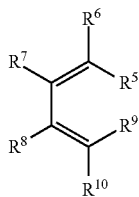

wherein $R^5$, $R^6$, $R^7$, $R^8$, $R^9$ and $R^{10}$ are each independently selected from the group consisting of H and $C_1$-$C_4$ alkyl or any of $R^6$ and $R^7$, $R^7$ and $R^8$, $R^8$ and $R^{10}$ or $R^5$ and $R^9$ may optionally be joined together to form a 5-, 6-, or 7-membered ring; providing a Lewis acidic ionic liquid to the reactor; and reacting the α,β-unsaturated carbonyl dienophile with the 1,3-diene to form a substituted cyclohexene product.

According to another embodiment, the present disclosure provides a process for producing a substituted cyclohexene product. The process comprises reacting mesityl oxide with piperylene in a Lewis acidic ionic liquid to form predominantly cis-1-(2,6,6-trimethylcyclohex-3-en-1-yl)ethanone. In certain embodiments, the 1-(2,6,6-trimethylcyclohex-3-en-1-yl)ethanone may be further converted to trans, trans-δ-damascone.

Still another embodiment of the present disclosure provides a process for producing (±)-δ-damascone. The process comprises reacting mesityl oxide with piperylene in a Lewis acidic ionic liquid to form predominantly cis-1-(2,6,6-trimethylcyclohex-3-en-1-yl)ethanone; epimerizing the cis-1-(2,6,6-trimethylcyclohex-3-en-1-yl)ethanone to trans-1-(2,6,6-trimethylcyclohex-3-en-1-yl)ethanone; and condensing the trans-1-(2,6,6-trimethylcyclohex-3-en-1-yl)ethanone with acetaldehyde to form (±)-δ-damascone. In certain embodiments, the Lewis acidic ionic liquid is selected from the group consisting of $AlCl_3$:[$C_2$mim]Cl, $AlCl_3$:[$C_8$mim]Cl, and mixtures thereof.

BRIEF DESCRIPTION OF DRAWINGS

The various non-limiting embodiments of this application may be better understood when read in conjunction with one or more of the following drawing figures.

FIG. 1 illustrates one approach for a Diels-Alder cycloaddition in a Lewis acidic ionic liquid according to the present disclosure.

FIG. 2 illustrates the effect of the amount of piperylene on a Diels-Alder cycloaddition according to one embodiment of the present disclosure.

DETAILED DESCRIPTION OF THE INVENTION

Definitions

As used herein, the term "comprising" means various components conjointly employed in the preparation of the compositions of the present disclosure. Accordingly, the terms "consisting essentially of" and "consisting of" are embodied in the term "comprising".

As used herein, the articles including "the", "a" and "an" when used in a claim or in the specification, are understood to mean one or more of what is claimed or described.

As used herein, the terms "include", "includes" and "including" are meant to be non-limiting.

As used herein, the term "plurality" means more than one.

As used herein, the term "Diels-Alder cycloaddition" describes a [4+2] cycloaddition between a diene component having a conjugated 1,3-diene functionality and a dienophile component having a reactive double or triple bond. Reactions via step-wise or concerted mechanisms are included within this term.

As used herein, the term "diene", when used in reference to a Diels-Alder cycloaddition, includes cyclic and acyclic compounds having a conjugated 1,3-diene moiety that can adopt an s-cis conformation.

As used herein, the term "dienophile" includes compounds having a reactive double or triple carbon-carbon bond that is reactive with a diene, for example, in a Diels-Alder cycloaddition.

As used herein, the term "Lewis acid" includes an electrophilic compound capable of accepting an electron pair.

As used herein, the term "ionic liquid" includes ionic compounds that are liquid under the reaction conditions.

As used herein, the term "Lewis acidic ionic liquid" includes complexes formed between a Lewis acid component and an ionic liquid component. For example, the Lewis acid component may be dissolved in the ionic liquid. Lewis acidic ionic liquids may be represented by the generic formula $M(A)_n$:[Cation]$^+$A$^-$, where the Lewis acid is represented by $M(A)_n$ and the ionic liquid is represented by [Cation]$^+$A$^-$.

As used herein, the term "piperylene" means a 1,3-diene having the IUPAC name 1,3-pentadiene.

As used herein, the term "mesityl oxide" means a compound having the IUPAC name 4-methyl-3-penten-2-one.

As used herein, the phrase "performed in a single reactor" means that the two or more reaction processes are performed in one (or more) reactor without an intermediate isolation step. In certain examples, the two or more reaction processes may also be performed without an intermediate workup or quenching step.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Lewis Acid Catalyzed Diels-Alder in Ionic Liquid

The present invention is related to processes for producing cyclic organic compounds using Lewis acidic ionic liquids. Specifically, substituted cyclohexene reaction products may be synthesized in Diels-Alder type cycloadditions using a diene and a dienophile under Lewis acidic ionic liquid conditions in the reaction medium. The processes disclosed herein have certain advantages over the prior art approaches, including, but not limited to, more concentrated reaction protocols, reduced side reactions, simplified workup conditions, recycling of reaction components, and fewer waste products. The processes disclosed herein may more readily be utilized on an industrial scale since equipment needs and solvents are reduced and process steps are eliminated. Thus, the processes disclosed herein provide distinct advantages over the prior art methods for synthesizing substituted cyclohexene reaction products.

The Diels-Alder cycloaddition involves a [4+2] reaction between a 1,3-diene and a dienophile to produce a cyclohexene product. Certain Diels-Alder cycloadditions may occur under thermal conditions. However, other Diels-Alder cycloadditions require a catalyst, such as a Lewis acid, for the diene to react with the dienophile to produce a cyclohexene product. Use of a Lewis acid catalysis in certain Diels-Alder cycloadditions may increase the regioselectivity of the reaction, extent of endo addition (i.e., diastereoselectivity), and in the case of enantioselective reactions, the extent of enantioselectivity. However, under standard conditions Lewis acid catalysis may have certain drawbacks, including, but not limited to, polymerization of reactants, more complicated workup protocols, lack of recycling of the catalyst, and disposal of metal containing waste products. Many of these drawbacks are highly undesired when performing reactions on an industrial scale. Thus, new protocols for using Lewis acid catalysis in Diels-Alder cycloadditions are needed.

Ionic liquids typically have melting temperatures of about 100° C. or less, or even 60° C. or less. Some ionic liquids exhibit no discernible melting point (based on DSC analysis) but are "flowable" at temperatures ranging from about 20° C. to about 100° C. An ionic liquid comprises an anionic component and a cationic component and neutral in overall charge. In liquid form, the cationic and anionic components of an ionic liquid may freely associate with one another (i.e., in a scramble). For example, when two or more ionic liquids are combined, the binary, ternary or more complex mixtures of ionic liquid components may be prepared. Such combinations are discussed in further detail in U.S. Application Publication Nos. 2004/0077519A1 and 2004/0097755A1. The mixtures of ionic liquids may have melting points of 100° C. or less. The various embodiments of the reactions herein may use ionic liquids, including mixtures of ionic liquids. Ionic liquids may be used in combination with a Lewis acid to form a Lewis acidic ionic liquid. Such combinations may display improved catalytic activity and reaction characteristics compared to the Lewis acid or the ionic liquid alone.

The present disclosure provides improved methods for the synthesis of substituted cyclohexenes utilizing a Diels-Alder reaction in a Lewis acidic ionic liquid. The present methods provide cyclohexenes that may be transformed in to compounds suitable for use as aroma or perfume ingredients. According to one embodiment, the process may comprise providing to a reactor an α,β-unsaturated carbonyl dienophile of Formula I:

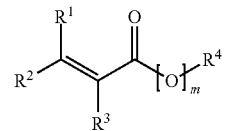

where m is 0 or 1 and $R^1$, $R^2$, $R^3$ and $R^4$ are as described herein; providing to the reactor a 1,3-diene of Formula II

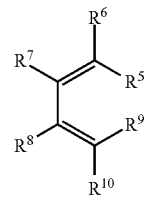

wherein $R^5$, $R^6$, $R^7$, $R^8$, $R^9$ and $R^{10}$ are as described herein; providing a Lewis acidic ionic liquid to the reactor; and reacting the α,β-unsaturated carbonyl dienophile with 1,3-diene to form a substituted cyclohexene product.

In certain embodiments, the dienophiles and/or dienes may be saturated or unsaturated, branched, unbranched or cyclic, which can be unsubstituted or mono- or polysubstituted. For example, the dienophile may be an α,β-unsaturated ketone, aldehyde, ester, amide, acid, or anhydride; and may be acyclic or cyclic. For example, in reference to Formula I, each of $R^1$, $R^2$, $R^3$ and $R^4$ may be independently selected from hydrogen, alkyl (such as $C_1$-$C_8$ alkyl or even $C_1$-$C_4$ alkyl), aromatic (e.g., phenyl) or halogen. In specific embodiments, each of $R^1$, $R^2$, $R^3$ and $R^4$ may be independently selected from hydrogen or $C_1$-$C_4$ alkyl. In other embodiments, two of the R groups, for example, $R^1$ and $R^2$, $R^1$ and $R^4$, $R^3$ and $R^4$, or $R^2$ and $R^3$, may optionally be joined together to form a cyclic structure, such as a 5-, 6-, or 7-membered ring. For example, $R^1$ and $R^2$, $R^1$ and $R^4$, $R^3$ and $R^4$, or $R^2$ and $R^3$ may be joined together by a 1, 2, 3, 4, or 5 atom chain comprising carbon atoms and, optionally heteroatoms to form a cyclic structure. The atoms in the chain may be substituted (for example, with one or more alkyl chains) or unsubstituted and may include various functionality, such as a carbonyl, lactone, lactam, anhydride, ether, amino or other functionality.

In specific embodiments, the dienophile may be an α,β-unsaturated carbonyl dienophile selected from the group consisting of 3-methyl-2-butenal, 3-methyl-2-butenoic acid, methyl 3-methyl-2-butenoate, ethyl 3-methyl-2-butenoate, sec-butyl 3-methyl-2-butenoate, tert-butyl 3-methyl-2-butenoate, (E)-2-butenoic acid, methyl (E)-2-butenoic acid, ethyl (E)-2-butenoic acid, sec-butyl (E)-2-butenoic acid, tert-butyl (E)-2-butenoic acid, (E)-2-butenal, 3-pentene-2-one (both E and Z isomers), 3-butene-2-one, 3-methyl-3-pentene-2-one (both E and Z isomers), and mesityl oxide. Dienophiles, such as the ones listed herein, may provide cyclohexene products from Diels-Alder cycloadditions that may be directly used as or readily converted to compounds useful as fragrance additives.

In reference to the diene structure in Formula II, according to various embodiments, each of $R^5$, $R^6$, $R^7$, $R^8$, $R^9$ and $R^{10}$ may be independently selected from hydrogen, alkyl (such as $C_1$-$C_4$ alkyl), alkoxy (such as $C_1$-$C_4$ alkoxy), siloxy (—OSi(alkyl)$_3$), aromatic (e.g., phenyl) or halogen. In specific embodiments, each of $R^5$, $R^6$, $R^7$, $R^8$, $R^9$ and $R^{10}$ may be independently selected from hydrogen or $C_1$-$C_4$ alkyl. In other embodiments, two of the R groups in Formula II, such as $R^6$ and $R^7$, $R^7$ and $R^8$, $R^8$ and $R^{10}$, or $R^5$ and $R^9$, may optionally be joined together to form a cyclic structure, such as a 5-, 6-, or 7-membered ring. For example $R^6$ and $R^7$, $R^7$ and $R^8$, $R^8$ and $R^{10}$, or $R^5$ and $R^9$ may be joined together by a 1, 2, 3, 4, or 5 atom chain comprising carbon atoms and, optionally heteroatoms to form a cyclic structure. The atoms in the chain may be substituted (for example, with one or more alkyl chains) or unsubstituted and may include various functionality, such as a carbonyl, lactone, lactam, anhydride, ether, amino or other functionality. Other cyclic structures corresponding to the general structures of Formula I and/or Formula II are within the subject matter of the present application. In specific embodiments, the 1,3-diene may be selected from the group consisting of piperylene, 2,4-hexadiene, 2-methyl-2,4-hexadiene, 4-methyl-1,3-pentadiene, cyclopentadiene, isoprene, and butadiene.

As recited above, the process of the present disclosure comprises providing a Lewis acidic ionic liquid. According to certain embodiments, the Lewis acidic ionic liquid may serve as both a solvent and a catalyst for the Diels-Alder [4+2] cycloaddition. In other embodiments, the Lewis acidic ionic liquid may be added in smaller quantities in the presence of an organic or inorganic solvent such that the Lewis acidic ionic liquid acts primarily as a catalyst for the Diels-Alder [4+2] cycloaddition. Specific ratios of the Lewis acid to the ionic liquid may display improved catalysis of the Diels-Alder cycloaddition.

For example, in specific embodiments, the Lewis acid ionic liquid complex may have a ratio of Lewis acid to ionic liquid ranging from 1:1 up to 4:1. In other embodiments, the Lewis acid to ionic liquid ration may range from about 1.1:1 to about 3:1, and even from about 1.5:1 to about 2:1. The ratio of Lewis acid to ionic liquid that produces the highest yield of cycloadduct may vary depending on the Lewis acid and the ionic liquid. For example, in embodiments where the Lewis acid is $AlCl_3$ and the ionic liquid is 1-ethyl-3-methylimidazolium chloride ("[emim]Cl" or "[$C_2$mim]Cl"), the Lewis acid to ionic liquid ratio for $AlCl_3$:[emim]Cl may range from about 1.1:1 to about 3:1, and even from about 1.5:1 to about 2:1. Alternatively, in embodiments where the Lewis acid is $AlCl_3$ and the ionic liquid is 1-methyl-3-octylimidazolium chloride ("[omim]Cl" or "[$C_8$mim]Cl"), the Lewis acid to ionic liquid ratio for $AlCl_3$:[omim]Cl may range from about 1:1 to about 3:1, and even from about 1.1:1 to about 2:1. In still other embodiments where the Lewis acidic ionic liquid comprises two Lewis acids, for example, $AlCl_3$:[$C_2$mim]Cl and $GaCl_3$:[$C_2$mim]Cl, the Lewis acid to ionic liquid ratio of each Lewis acidic ionic liquid may be independent of the other. In specific embodiments, the greatest yields in this embodiment are observed when the molar fraction of Lewis acid to the ionic liquid ranges from 0.6 to 0.7.

In certain embodiments, the Lewis acidic ionic liquid has a structure:

$M(A)_n$:[Cation]$^+$A$^-$.

According to this structure for the Lewis acidic ionic liquid, the Lewis acid component is represented by $M(A)_n$, where M is may be a metal such as a transition metal, an alkali earth metal, an alkali metal, a lanthanide metal, or another metal, such as aluminum, gallium, germanium, indium, thallium, strontium, bismuth and the like; A is a non-metal component, such as a alkyl, halogen, alkoxy or anionic component; and n is an integer corresponding to the valence of M, for example, in certain embodiments, n is an integer ranging from 2 to 4. The metal may be a metal such as Ti, Ni, Ru, Nd, Sc, Y, Al, Ga, In, Zn, Sm, and Zr. In specific embodiments, the metal M may be selected from the group consisting of Al, Ga, In, Zn, and Zr or in particular embodiments, Al, Ga, and In. The non-metal part of the Lewis acid, A, may be selected from a variety of non-metal counterparts of Lewis acids, such as alkoxy, alkyl, methane sulfonate ("mesylate", $CH_3SO_3^-$), trifluoromethane sulfonate ("triflate" or "OTf", $CF_3SO_3^-$), p-toluene sulfonate ("tosylate", $CH_3C_4H_4SO_3^-$), Cl, Br, or I. In specific embodiments the non-metal counterpart of the Lewis acid is selected from the group consisting of Cl, Br, I, and $CF_3SO_3^-$ or in particular embodiments, Cl and $CF_3SO_3^-$. According to the structure of the Lewis acidic ionic liquid, the ionic liquid component is represented by [Cation]$^+$A$^-$, where [Cation]$^+$ is the cationic component of the ionic liquid and A$^-$ is the anionic component of the ionic liquid. In the various embodiments of the Lewis acidic ionic liquids described herein, the anionic component of the ionic liquid is typically the same as the non-metal component of the Lewis acid, however, it should be noted that Lewis acidic ionic liquids where the anionic component of the ionic liquid is different that the non-metal component of the Lewis acid are also contemplated for the Lewis acidic ionic liquids used herein.

Although a variety of Lewis acids have been used as catalysts in conventional Diels-Alder cycloadditions, including, but not limited to, $InCl_3$, $Al(OTf)_3$, $SnCl_4$, $ZnCl_2$, $Zn(OTf)_2$, $TiCl_4$, $Ti(OAlkyl)_4$, $Y(OTf)_3$, $ZrCl_4$, $NdCl_3$, $SmCl_3$, $RuCl_3 \cdot xH_2O$ and $NiCl_2 \cdot 6H_2O$; the chloroaluminate compounds, such as, for example, $AlCl_3$, (alkyl)$AlCl_2$, and (alkyl)$_2$AlCl, have proven to be effective catalysts for a Diels-Alder reaction under certain reaction conditions. However, certain chloroaluminate compounds may be sensitive to moisture. Other Lewis acid catalysts that may display better moisture sensitivity include Lewis acids comprising elements from the same group of the periodic table as aluminum, for example, gallium and indium. The reactivity and moisture sensitivity of Lewis acids comprising these elements in the Diels-Alder reactions decreases in the following order: aluminum>gallium>indium. In certain embodiments of the present disclosure, the Diels-Alder cycloaddition in a Lewis acidic ionic liquid comprising $AlCl_3$ showed greater reactivity than the Diels-Alder cycloaddition in a Lewis acidic ionic liquid comprising $GaCl_3$. Thus, in certain embodiments, it may be advantageous to utilize a mixture of Lewis acids. For example, in certain embodiments, the Lewis acidic ionic liquid may comprise a mixture of Lewis acids, for example, $AlCl_3$ and $GaCl_3$.

As discussed herein the ionic liquid component of the Lewis acidic ionic liquid may be represented by [Cation]$^+$A$^-$. According to various embodiments, "Cation" represented the cationic component of the ionic liquid and may be any cationic component suitable for ionic liquids. For example, according to various embodiments, the cationic component may comprise a cationic nitrogen, such as, a quaternary ammonium cation (i.e., $R_4N^+$, where R is alkyl), an iminium cation (i.e., an $sp^2$ cationic nitrogen having a double bond and two single bonds, $R_2(N^+)=R$ where R is alkyl), or an aryliminium cation (i.e., an $sp^2$ cationic nitrogen where the nitrogen is part of an aromatic ring, for example, an alkylated pyridinium cation). In other embodiments, the cationic component may comprise a cationic sulfur, such as a trialkylsulfonium cation (i.e., $R_3S^+$) or a cationic phosphorus, such as a tetraalkylphosphonium cation (i.e., $R_4P^+$).

In specific embodiments, the cationic component of the ionic liquid may comprise a cationic nitrogen or a cationic phosphorus. For example, according to certain embodiments, the cationic component (i.e., the "Cation") may be a quaternary ammonium cation, choline, a tetraalkylphosphonium cation, or a nitrogen containing heterocyclic or heteroaromatic cation, such as, but not limited to, an N,N-dialkylimidazolium cation, a N,N-dialkylpyrazolium cation, a 1,2-dialkyl-1,2,3-triazolium cation, a 1,3-dialkyl-1,2,3-triazolium cation, a 1,4-dialkyl-1,2,4-triazolium cation, an N-alkyl-1,3-oxazolium cation, an N-alkyl-1,3-thiazolium cation, an N-alkylpyridinium cation, an N-alkylpyridazinium cation, an N-alkylpyrimidinium cation, an N-alkylpyrazinium cation, an N-alkylquinolinium cation, an N-alkylisoquinolinium cation, N,N-dialkylpiperidinium cation, an N,N-dialkylpyrroidinium cation, or an N,N-dialkylmorpholinium cation. In specific embodiments, the cationic component of the ionic liquid may be an N,N-dialkylimidazolium cation, such as an 1-($C_2$-$C_8$)alkyl-3-methylimidazolium cation. In other embodiments, the cationic component ("Cation") of the ionic liquid may be a cationic compound having a structure selected from the group shown in Scheme 2. According to these cationic structures, the substituents $R^{11}$ through $R^{22}$ may be any suitable substituent, such as but not limited to, linear or branched, substituted or unsubstituted, cyclic or acyclic, and/or saturated or unsaturated alkyl, hydroxyalkyl, haloalkyl, alkoxyalkyl, phenyl, aryl or heteroaryl. According to particular embodiments, $R^{11}$ through $R^{22}$ may each independently be a substituent selected from the group consisting of —H, —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, ($C_2$-$C_6$)alkenyl, hydroxyalkyl, haloalkyl, alkoxyalkyl, ($C_6$-$C_{10}$)aryl, and ($C_8$-$C_{16}$)alkenylaryl.

Scheme 2

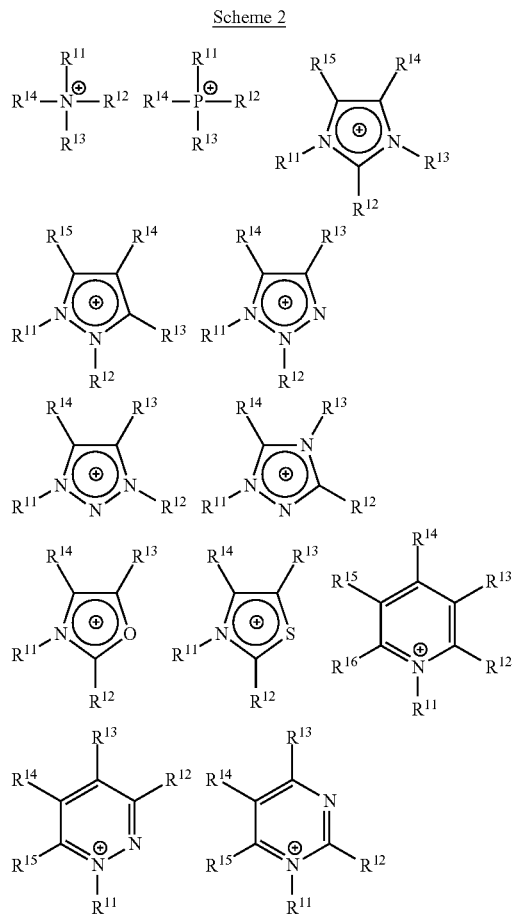

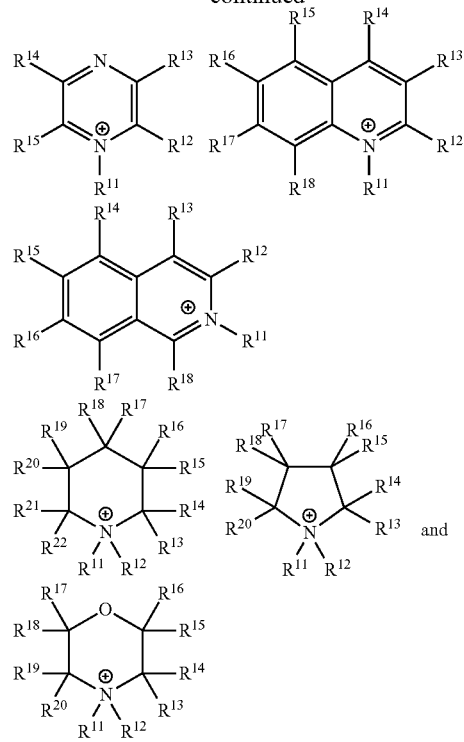

In certain embodiments, the length of the substituent chains (e.g., any of $R_{11}$ through $R^{22}$) in the cationic structures may range from $C_2$-$C_{14}$ and in other embodiments from $C_2$-$C_8$. For example, in certain embodiments, the Lewis acidic ionic liquid may be selected from the group consisting of $AlCl_3$:[$C_n$mim]Cl; $GaCl_3$:[$C_n$mim]Cl; $ZrCl_4$:[$C_n$mim]Cl; $Al(OTf)_3$:[$C_n$mim][OTf]; and mixtures of any thereof, wherein n is an integer from 2 to 8. That is, in certain embodiments, the cationic component of the ionic liquid +may be 1-ethyl-3-methylimidazolium ion, 1-propyl-3-methylimidazolium ion, 1-butyl-3-methylimidazolium ion, 1-pentyl-3-methylimidazolium ion, 1-hexyl-3-methylimidazolium ion, 1-heptyl-3-methylimidazolium ion, or 1-octyl-3-methylimidazolium ion. The length of the side chain in the cationic component of the ionic liquid may affect a variety of characteristics the Diels-Alder cycloaddition, such as, for example, reagent solubility, separation ease, stereoselectivity, diastereoselectivity, cycloadduct yield, and the like. For example, in one particular embodiment involving the Diels-Alder cycloaddition of mesityl oxide and piperylene, a Lewis acidic ionic liquid comprising $AlCl_3$:[$C_8$mim]Cl displayed a higher yield of the desired cycloadduct than a similar Diels-Alder cycloaddition of mesityl oxide and piperylene utilizing the Lewis acidic ionic liquid comprising $AlCl_3$:[$C_2$mim]Cl. Without intending to be bound to any particular theory, the longer side chain in the imidazolium ionic liquid is believed to increase the solubility of the starting materials in the ionic liquid.

With reference to the anionic component of the ionic liquid, $A^-$, the anionic component may be any suitable counter anion for the cationic component of the ionic liquid. For example, certain suitable anionic components include, but are not limited to, halide anions (i.e., $F^-$, $Cl^-$, $Br^-$, or $I^-$), methane sulfonate ("mesylate", $CH_3SO_3^-$), trifluoromethane sulfonate ("triflate" or "OTf", $CF_3SO_3^-$), p-toluene sulfonate ("tosylate", $CH_3C_4H_4SO_3^-$), hydrogen sulfate ($HOSO_3^-$), alkyl sulfate (alkylOSO$_3^-$), hexafluorophosphate (PF6$^-$), tetrafluoroborate (BF$_4^-$), bistriflimide ((CF$_3$SO$_2$)$_2$N$^-$), hexafluoroantimonate (SbF6$^-$), thiocyanate (SCN$^-$), nitrate (NO$_3^-$), acetate (CH$_3$COO$^-$), trifluoroacetate (CF$_3$COO$^-$), dicyanimide ((CN)$_2$N$^-$), dialkylphosphate ((alkylO)$_2$PO$_2^-$), carbonate (HOCO$_2^-$), alkylcarbonate (alkylOCO$_2^-$), or tris(trifluoromethylsulfonyl)methide ((triflyl)$_3$C$^-$). Other anion components of ionic liquids are known in the art and could be utilized in the methods disclosed herein. In specific embodiments, the anionic component of the ionic liquid may be halide, such as chloride (Cl$^-$), bromide (Br$^-$) or iodide (I$^-$); or trifluoromethane sulfonate ("triflate" or "OTf", CF$_3$SO$_3^-$) and in particular embodiments, chloride or trifluoromethane sulfonate.

As discussed herein, in certain embodiments, it may be desirable for the anionic component of the ionic liquid to be the same as the non-metal component of the Lewis acid. For example, in specific embodiments, the anionic component of the ionic liquid and the non-metal component of the Lewis acid may both be chloride, bromide, or triflate. When the anionic component of the ionic liquid is the same as the non-metal component of the Lewis acid, cross contamination is minimized and recycling of the ionic liquid and/or the Lewis acid is possible.

Suitable Lewis acidic ionic liquids that may be used to catalyze the Diels-Alder cycloadditions described herein include, but are not limited to, AlCl$_3$:[C$_2$mim]Cl; AlCl$_3$:[C$_8$mim]Cl; InCl$_3$:[C$_2$mim]Cl; InCl$_3$:[C$_8$mim]Cl; ZnCl$_2$:[C$_2$mim]Cl; ZnCl$_2$:[C$_8$mim]Cl; ZrCl$_4$:[C$_2$mim]Cl; ZrCl$_4$:[C$_8$mim]Cl; NdCl$_3$:[C$_2$mim]Cl; NdCl$_3$:[C$_8$mim]Cl; SmCl$_3$:[C$_2$mim]Cl; SmCl$_3$:[C$_8$mim]Cl; RuCl$_3$.xH$_2$O:[C$_2$mim]Cl; RuCl$_3$.xH$_2$O:[C$_8$mim]Cl; Al(OTf)$_3$:[C$_2$mim][OTf]; Al(OTf)$_3$:[C$_8$mim][OTf]; Y(OTf)$_3$:[C$_2$mim][OTf]; Y(OTf)$_3$:[C$_6$mim][OTf]; Y(OTf)$_3$:[C$_8$mim][OTf]; Zn(OTf)$_2$:[C$_2$mim][OTf]; Zn(OTf)$_2$:[C$_8$mim][OTf]; and various combinations or mixtures thereof. As discussed herein, "C$_2$mim" means 1-ethyl-3-methylimidazolium, "C$_6$mim" means 1-hexyl-3-methylimidazolium" and "C$_8$mim" means 1-methyl-3-octyl-imidazolium. In certain embodiments, the Lewis acidic ionic liquid is selected from the group consisting of AlCl$_3$:[C$_2$mim]Cl; AlCl$_3$:[C$_8$mim]Cl; GaCl$_3$:[C$_2$mim]Cl; ZrCl$_4$:[C$_2$mim]Cl; ZrCl$_4$:[C$_8$mim]Cl; Al(OTf)$_3$:[C$_2$mim][OTf]; Al(OTf)$_3$:[C$_8$mim][OTf]; and mixtures of any thereof.

As described herein, the Diels-Alder cycloaddition involves a reaction between a 1,3-diene and a dienophile to produce a substituted cyclohexene. In particular examples, the dienophile may be an α,β-unsaturated carbonyl dienophile (that is the dienophile includes a carbon-carbon double bond in conjugation with a carbon-oxygen double bond). In one embodiment of the present disclosure, the α,β-unsaturated carbonyl dienophile is mesityl oxide and the 1,3-diene is piperylene. According to this embodiment, the mesityl oxide reacts with the piperylene in a Diels-Alder cycloaddition to give a substituted cyclohexene. As discussed herein, this Diels-Alder cycloaddition may be catalyzed by a Lewis acid. However, prior art examples of Lewis acid catalyzed Diels-Alder cycloadditions of mesityl oxide and piperylene suffer from low yields and significant polymer formation. Under the present process, the mesityl oxide and piperylene undergo a facile Diels-Alder cycloaddition in the presence of a Lewis acidic ionic liquid, such as those described herein. In specific embodiments, the Lewis acidic ionic liquid may be AlCl$_3$:[C$_2$mim]Cl; AlCl$_3$:[C$_8$mim]Cl; or mixtures thereof.

According to certain embodiments of producing substituted cyclohexenes, the substituted cyclohexene product may comprise a mixture of cis- and trans-1-(2,6,6-trimethylcyclohex-3-en-1-yl)ethanone where the methyl substituent at the C2 ring carbon and the ethyl ketone substituent at the C1 ring carbon are on the same face (i.e., cis) or the opposite face (i.e., trans) of the cyclohexene ring. In specific embodiments, the substituted cyclohexene product may comprise predominantly cis-1-(2,6,6-trimethylcyclohex-3-en-1-yl)ethanone, with the minor cycloaddition component comprising the trans-1-(2,6,6-trimethylcyclohex-3-en-1-yl)ethanone. For example, in certain embodiments of the Diels-Alder cycloaddition the cis to trans ratio of the 1-(2,6,6-trimethylcyclohex-3-en-1-yl)ethanone may be greater than 10:1. The structure of 1-(2,6,6-trimethylcyclohex-3-en-1-yl)ethanone is shown in Formula III.

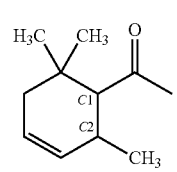

III

According to still other embodiments, the process for producing substituted cyclohexenes of the present disclosure may further comprise the step of purifying the substituted cyclohexene product. According to these embodiments, any conventional method of purification may be used.

For example, in those embodiments where the substituted cyclohexene product is a solid, the substituted cyclohexene product may be purified, for example, by crystallization or recrystallization. Crystallization or recrystallization using a single solvent or mixed solvent system are contemplated. In those embodiments, where the substituted cyclohexene product is a liquid or a low melting solid, the substituted cyclohexene product may be purified using a distillation method, such as, but not limited to simple distillation, steam distillation, fractional distillation, azeotropic distillation, spinning band distillation, vacuum or reduced pressure distillation, and combination of these methods (for example, vacuum fractional distillation). In still other embodiments, the substituted cyclohexene product may be purified by chromatographic methods, such as, but not limited to column chromatography, liquid chromatography, flash chromatography, medium pressure liquid chromatography, high performance liquid chromatography (HPLC), thin layer chromatography, reverse-phase chromatography, and combinations of these methods. Alternatively, the substituted cyclohexene may be purified by using a combination of any of the above referenced purification methods.

Still further embodiments of the processes for producing substituted cyclohexenes may further comprise converting to substituted cyclohexene to a desired product by one or more further chemical transformations. For example, in certain embodiments, the process may further comprise converting the substituted cyclohexene product to a product useful as a perfume, fragrance or aroma enhancing compound or product. Suitable fragrance enhancing products that may be produced by the substituted cyclohexene products of the present disclosure include, but are not limited to, fragrance products selected from the group consisting of (±)-(E)-α-damascone, (±)-(E)-β-damascone, (±)-(E)-δ-damascone, (±)-(E)-γ-damascone, 1-(2,2,6-trimethylcyclohexyl)-2-buten-1-one, 1-(2,2,6-trimethylcyclohexyl)-1-butanone, trans-4-(2,2,6-trimethylcyclohexyl)-3-buten-2-one, (±)-(E)-α-ionone, (±)-(E)-γ-ionone, (±)-dihydro-α-ionone, (±)-dihydro-γ-ionone, (±)-tetrahydroionone, methyl (±)-α-cyclogeranate, methyl (±)-β-cyclogeranate, ethyl (±)-(β-cyclogeranate, ethyl (±)-β- safranate, methyl 2,2-dimethyl-δ-methylenecyclohexane-1-carboxylate, ethyl 2,2-dimethyl-δ-methylenecyclohexane-1-carboxylate, methyl 2,6,6-trimethyl-3-cyclohexene-1-carboxylate, ethyl 2,6,6-trimethylcyclohexane-1-carboxylate, 1-(2',2',6'-trimethylcyclohexyl)-3-pentanone, 1-(2',2',6'-trimethylcyclohexyl)-3-hexanone, 1-(2',2',6'-trimethylcyclohexyl)ethanone, (±)-dihydro-β-ionol, (±)-β-irone, (±)-γ-irone, (±)-α-irone, 2,4,6-trimethyl-3-cyclohexene-1-carbaldehyde, β-ionone, damascenone, γ-methyl ionone, (β-methyl ionone, and any of these compounds wherein the C═O has been replaced with a CH—OH moiety.

In other embodiments where the substituted cyclohexene product comprises 1-(2,6,6-trimethylcyclohex-3-en-1-yl)ethanone, such as a mixture of cis- and trans-1-(2,6,6-trimethylcyclohex-3-en-1-yl)ethanone, the process for producing a substituted cyclohexene may further comprise converting the 1-(2,6,6-trimethylcyclohex-3-en-1-yl)ethanone to (±)-δ-damascone which has a structure represented by Formula IV:

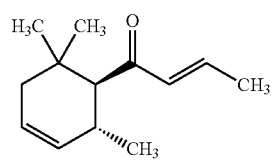

IV

Methods of converting the 1-(2,6,6-trimethylcyclohex-3-en-1-yl)ethanone may include the following chemical transformations: epimerizing the cis-1-(2,6,6-trimethylcyclohex-3-en-1-yl)ethanone to trans-1-(2,6,6-trimethylcyclohex-3-en-1-yl)ethanone; condensing the trans-1-(2,6,6-trimethylcyclohex-3-en-1-yl)ethanone with acetaldehyde to form (±)-δ-damascone. According to these embodiments, epimerizing the cis-1-(2,6,6-trimethylcyclohex-3-en-1-yl)ethanone to the trans isomer may be affected by reacting the cis-1-(2,6,6-trimethylcyclohex-3-en-1-yl)ethanone with a base, for example, potassium hydride or a metal alkoxide base, such as potassium tert-butoxide. Other bases known in the art may also be suitable for epimerizing the cis isomer to the trans-1-(2,6,6-trimethylcyclohex-3-en-1-yl)ethanone.

According to various embodiments, the trans-1-(2,6,6-trimethylcyclohex-3-en-1-yl)ethanone may be condensed with acetaldehyde to form (±)-δ-damascone. In this embodiment, the trans-1-(2,6,6-trimethylcyclohex-3-en-1-yl)ethanone may condense with the acetaldehyde via an aldol condensation (i.e., reaction of the enolate of the ketone with acetaldehyde to form the aldol addition product followed by a dehydration) to form the (±)-δ-damascone. The condensing step for the trans-1-(2,6,6-trimethylcyclohex-3-en-1-yl)ethanone may also be performed with another aldehyde or ketone reagent to form a condensation product. In these embodiments, the condensation products (i.e., aldol reaction and, optionally the elimination reaction) will be other cyclohexene products of interest, such as cyclohexene products with different fragrances. The processes may further comprise purifying the condensation product, for example, but a purification method selected from crystallization, distillation or chromatography. Suitable examples of these purification methods are described herein in reference to purifying the Diels-Alder cycloaddition product.

In specific embodiments, the epimerization step and the condensation step may be performed in a single reactor. As used herein, the phrase "single reactor" means that two or more chemical transformations are performed without an intermediate isolation or workup step. For example, according to these embodiments, the mixture or cis- and trans-1-(2,6,6-trimethylcyclohex-3-en-1-yl)ethanone may be submitted to epimerization conditions and once the epimerization is substantially complete, the reaction solution comprising substantially all trans-1-(2,6,6-trimethylcyclohex-3-en-1-yl)ethanone is subjected directly to the condensation conditions by adding the aldehyde to the epimerization product. Non-limiting examples of performing the epimerization step and the condensing step in a single reactor are described in detail in co-pending U.S. Provisional Application identified by Attorney Docket No. 11213P, entitled "Processes for Epimerizing Cyclohexenyl Ketones with Subsequent Aldol Condensation to Produce Fragrance Compounds", filed on a date even with the present application and assigned to The Procter & Gamble Company, Cincinnati, Ohio.

Specific embodiments of the present disclosure provide a process for producing a substituted cyclohexene product comprising reacting mesityl oxide with piperylene in an Lewis acidic ionic liquid to form predominantly cis-1-(2,6,6-trimethylcyclohex-3-en-1-yl)ethanone. The Lewis acidic ionic liquid may be any of the Lewis acidic ionic liquids discussed herein. In certain embodiments, the Lewis acidic ionic liquid may be $AlCl_3$:[$C_2$mim]Cl; $AlCl_3$:[$C_8$mim]Cl; $GaCl_3$:[$C_2$mim]Cl; $ZrCl_4$:[$C_2$mim]Cl; $ZrCl_4$:[$C_2$mim]Cl; $Al(OTf)_3$:[$C_2$mim][OTf]; $Al(OTf)_3$:[$C_8$mim][OTf]; or mixtures of any thereof. As recited herein, the ratio of Lewis acid to ionic liquid may be any ratio described herein as suitable, for example, a Lewis acid to ionic liquid ratio ranging from 1:1 to 4:1.

Other embodiments of the process comprising reacting mesityl oxide with piperylene in an Lewis acidic ionic liquid to form predominantly cis-1-(2,6,6-trimethylcyclohex-3-en-1-yl)ethanone may further comprise converting the cis-1-(2,6,6-trimethylcyclohex-3-en-1-yl)ethanone to (±)-δ-damascone. In specific embodiments, the process comprising reacting mesityl oxide with piperylene in an Lewis acidic ionic liquid to form predominantly cis-1-(2,6,6-trimethylcyclohex-3-en-1-yl)ethanone may further comprise epimerizing the cis-1-(2,6,6-trimethylcyclohex-3-en-1-yl)ethanone to trans-1-(2,6,6-trimethylcyclohex-3-en-1-yl)ethanone and condensing the trans-1-(2,6,6-trimethylcyclohex-3-en-1-yl)ethanone with an aldehyde to form a condensation product. The process may further comprise purifying the condensation product, as described herein. For example, in certain embodiments, the aldehyde may be acetaldehyde when the condensation product is (±)-δ-damascone, which may then optionally be purified, for example, by a distillation process. As discussed herein, in one embodiment, the epimerizing step and the condensing step may be performed in a single reactor.

In still a further embodiment, the present disclosure provides a process for producing (±)-δ-damascone. The process may comprise reacting mesityl oxide with piperylene in a Diels-Alder cycloaddition in a Lewis acidic ionic liquid to form predominantly cis-1-(2,6,6-trimethylcyclohex-3-en-1-yl)ethanone; epimerizing the cis-1-(2,6,6-trimethylcyclohex-3-en-1-yl)ethanone to trans-1-(2,6,6-trimethylcyclohex-3-en-1-yl)ethanone; and condensing the trans-1-(2,6,6-trimethylcyclohex-3-en-1-yl)ethanone with acetaldehyde to form (±)-δ-damascone. The Lewis acidic ionic liquid may be any of those described herein and in specific embodiments may be $AlCl_3$:[$C_2$mim]Cl; $AlCl_3$:[$C_8$mim]Cl; or mixtures thereof. As described herein, the epimerizing step and the condensing step may be performed in a single reactor vessel.

The novel process for producing substituted cyclohexenes described herein may improve the yield of the desired cyclohexene compounds without the use of volatile solvents and without significant formation of by-products. In addition, the Diels-Alder cycloaddition of mesityl oxide and piperylene in $AlCl_3$:[$C_2$mim]Cl; $AlCl_3$:[$C_8$mim]Cl; or mixtures thereof may be particularly suitable for the industrial production of substituted cyclohexene reaction products considering the increased efficiency of producing the cis-isomer of the cycloadduct. Additionally, the reagents and reaction conditions have been designed such that the recycling of the catalyst may be achieved.

In certain embodiments, a proper amount of solvent may be used in conducting the Diels-Alder cycloaddition. Many standard organic or inorganic solvents may be suitable for use in the processes described herein, however, the solvents used in the reaction may affect the yield of the reaction and stereoselectivity of the reaction products. Typically, solvents can comprise from about 50% to about 95% by weight of the reaction mixture. Suitable solvents include ionic, polar or non-polar; organic or inorganic solvents, for example, but not limited to, aromatic solvents, such as, but not limited to, toluene; halogenated solvents, such as, but not limited to, dichloromethane, ionic liquids [$C_2$mim][$NTf_2$], and water. In other embodiments, the Diels-Alder reaction may be performed neat or with the Lewis acidic ionic liquid acting as the solvent.

The effectiveness of the Lewis acidic ionic liquids to generate the desired cyclic organic compounds may depend, at least in part, on the reaction conditions and the specific Lewis acid and ionic liquid used in the reaction. The properties of the Lewis acidic ionic liquids utilized in the processes described herein, e.g., the Lewis acidity, may be adjusted by changing the ratio of the metal salt in the ionic liquid. For example, the ratio of the Lewis acid to the ionic liquid may affect the stereochemistry of the reaction products, for example, the exo and endo ratio of the Diels-Alder cycloaddition products.

In the Diels-Alder cycloadditions of the present disclosure, the ratio of the $\alpha,\beta$-unsaturated carbonyl dienophile to 1,3-diene may have an effect on the yield of the cycloadduct. Typically, the 1,3-diene was used in excess due to competing polymerization of the diene. However, if the 1,3-diene is used in too large an excess, isolation of the cycloaddition product may be complicated by formation of significant polymer co-product. In certain embodiments, the ratio of the $\alpha,\beta$-unsaturated carbonyl dienophile to 1,3-diene may range from about 1:2 to about 1:10. In specific embodiments, the 1,3-diene may be used in excess, for example, where the ratio of the $\alpha,\beta$-unsaturated carbonyl dienophile to 1,3-diene ranges from 1:2 to 1:6, or in other embodiments, from 1:3 to 1:5. For example in the Diels-Alder cycloaddition of mesityl oxide and piperylene in a Lewis acidic ionic liquid comprising $AlCl_3$:[$C_2$mim]Cl (Lewis acid:ionic liquid ration, 1.5:1.0), the ratio of the $\alpha,\beta$-unsaturated carbonyl dienophile to 1,3-diene may range from about 1:2 to about 1:10 and in certain embodiments, from 1:3 to 1:6 or even around 1:5. Referring now, to FIG. 2, the effect of changes in the dienophile to diene ratio on yield for the Diels-Alder cycloaddition of mesityl oxide and piperylene is presented. As shown in FIG. 2, decreasing the amount of piperylene in a Lewis acidic ionic liquid comprising $AlCl_3$ significantly decreased the yield of the reaction. Therefore, an excess of piperylene relative to mesityl oxide may increases the yield of the Diels-Alder cycloaddition and may counter the undesirable self polymerization of piperylene.

The Lewis acidic ionic liquids that catalyze the Diels-Alder cycloadditions may also catalyze the undesirable polymerization of the starting materials. For example, polymerization of the dienophile and/or the 1,3-diene may reduce the overall yield of the Diels-Alder cycloadduct. Therefore, the reaction conditions may have a critical effect on the yield and efficiency of the Diels-Alder reaction and may also influence the kinetics and thermodynamics of the undesirable polymerization of the starting materials. The reaction conditions of the present disclosure have been carefully selected to increase the yield and efficiency of the Diels-Alder reaction and reduce the undesirable polymerization of the starting materials. The reaction conditions that may have a critical effect on the yield and efficiency of the Diels-Alder reaction include, for example, but not limited to, the reaction temperature, pressure, pH, atmosphere, and time; the addition speed of reagents to the reaction mixture, the ratio of reagents, and the effect of any solvents, such as the effect of water.

For example, the reaction rate of the Diels-Alder reaction and competing side reactions, such as the polymerization of starting materials, may increase with the addition speed of the reagents to the reaction mixture, reaction temperature, and reaction time. In certain embodiments, the 1,3-diene reagent may be added slowly to the reaction mixture at a rate ranging from about 0.1 mL/min to about 1 mL/min, and in other embodiments from about 0.25 mL/min to about 0.75 mL/min and in still other embodiments from about 0.5 mL/min to about 0.625 mL/min. The proper addition speed of the 1,3-diene reagent may be important for increasing yield and efficiency of the Diels-Alder cycloaddition. For example, rapid addition of the reagents to the reaction mixture may result in a violent, exothermic reaction that may result in an increase in the reaction temperature and promote the undesirable polymerization of the starting materials. In certain embodiments, the reagents may be added slowly to the reaction mixture at a slow rate to reduce the temperature rise associated with the exothermic reaction and, thus, minimize the undesirable polymerization of the starting materials.

Temperature of the Diels-Alder cycloaddition process may also have an effect on the efficiency of the reaction. In certain embodiments, the reaction temperature ranges from about −25° C. to about 110° C. Increased reaction temperature, including, for example, the exothermic reaction resulting from the addition of the reagents to the reaction mixture, may promote the undesirable polymerization of the starting materials. In certain embodiments, the temperature of the reaction mixture when the dienophile is added to the solution comprising the Lewis acidic ionic liquid may range from about 16° C. to about 110° C., and in other embodiments from about 16° C. to about 80° C., and in even further embodiments from about 16° C. to about 60° C. According to one specific embodiment, the temperature of the reaction mixture when the dienophile is added to the Lewis acidic ionic liquid may range from about 16° C. to about 20° C. The complex formed between the dienophile and the Lewis acidic ionic liquid may then be cooled prior to addition of the 1,3-diene. In certain embodiments, the reaction temperature when the 1,3-diene is added to the reaction mixture comprising the complex of the dienophile and the Lewis acidic ionic liquid may range from about −20° C. to about 20° C., and in some embodiments from about −20° C. to about 0° C. In specific embodiments, the reaction temperature when the 1,3-diene is added to the reaction mixture ranges from about −20° C. to about −18° C.

Any sudden increase in the reaction temperature, for example, removing the cooling bath immediately after the addition of the piperylene, may significantly increase the undesirable polymerization of the starting materials. However, the yield and efficiency of the Diels-Alder reaction may be decreased if the reaction mixture is overcooled such that complexation of the reagents is diminished. Therefore, the proper reaction temperature at each step of the process may be important to increase the yield of the reaction and decrease the undesirable polymerization of the starting materials.

In certain embodiments, the reaction time may range from about 0.5 hour to about 240 hours, and in other embodiments from about 5 hours to about 180 hours, and in still other embodiments from about 24 hours to about 80 hours. The reaction time may be important to increasing yield and efficiency of the Diels-Alder reaction. For example, under certain reaction conditions, the Diels-Alder cycloadduct and/or reactants may further undergo undesirable reactions that generate undesirable products and reduces its yield.

The yield and efficiency of the Diels-Alder reaction may also be affected by the quality of the Lewis acidic and ionic liquids. For example, certain chloroaluminate Lewis acid catalysts and ionic liquids may be sensitive to moisture and should be prepared, stored, and used under nitrogen. In certain embodiments, an amount of a proton scavenger, for example, a base, such as an amine base, for example, but not limited to, triethylamine, Hunig's base (diisopropyl ethyl amine), and the like, may be added to the Diels-Alder reaction mixture to improve the effectiveness of the cycloaddition, for example, by neutralizing protic acids, such as hydrochloric acid produced by partially hydrolyzed Lewis acid catalysts. Protic acids may catalyze polymerization of $\alpha,\beta$-unsaturated carbonyl compounds and/or 1,3-dienes, so adding a proton scavenger may increase the yield of the reaction by decreasing the undesirable polymerization of the starting materials. In certain embodiments, the amount of proton scavenger, such as Hunig's base, added to the reaction mixture may range from about 2 molar percent to about 10 molar percent.

In certain embodiments, the Lewis acid and/or ionic liquid used in the Diels-Alder reaction may be recycled. Recycling one or more of the Lewis acid and the ionic liquid may significantly reduce the cost and reduce and/or eliminate the formation of waste products, such as hydrolysis products, for example, the $Al(OH)_3$ solid waste that is generated when $AlCl_3$ is used. This may increase the industrial utility of the processes described herein. In one prophetic example of the Diels-Alder cycloaddition process, the cycloadduct products may be isolated from the ionic liquid without the use of water. This may allow for the recovery and reuse of the Lewis acid, ionic liquid or both. According to this embodiment, the isolation process may comprise treating the reaction products with an excess of a compound that generates an ionic liquid phase comprising the Lewis acid and ionic liquid, extracting the Lewis acid and ionic liquid into an immiscible organic solvent, and evaporating the organic solvent. The Lewis acid and/or ionic liquid may then be recycled.

While various specific embodiments have been described in detail herein, the present disclosure is intended to cover various different combinations of the disclosed embodiments and is not limited to those specific embodiments described herein. The various embodiments of the present disclosure may be better understood when read in conjunction with the following representative examples. The following representative examples are included for purposes of illustration and not limitation.

The compounds of the present invention are prepared according to methods which are well-known to those skilled in the art. The starting materials used in preparing the compounds of the invention are well-known to those skilled in the art, made by known methods, or are commercially available.

EXAMPLES

Example 1

Lewis Acid Catalyzed Diels-Alder Cycloaddition

In this example, a substituted cyclohexene product comprising predominately cis-1-(2,6,6-trimethylcyclohex-3-en-1-yl)ethanone is formed. The $\alpha,\beta$-unsaturated carbonyl dienophile is mesityl oxide, the 1,3-diene is piperylene, and the Lewis acidic ionic liquid is $AlCl_3:[C_2mim]Cl$.

One equivalent of mesityl oxide (50 mmol; 5.7 mL) is added slowly with vigorous stirring at room temperature (16-19° C.) under nitrogen atmosphere to 2.15 equivalents (15.0 g) of freshly prepared $AlCl_3:[C_2mim]Cl$ (Lewis acid to ionic liquid ration=1.5:1.0). The mixture is stirred at room temperature for 1 hour. Five equivalents of piperylene (250 mmol; 25 mL) is added slowly to the reaction mixture at 0° C. with vigorous stirring and ice cooling over 40 min. The reaction is allowed to slowly warm to room temperature and stirred at room temperature for 6 days. The mixture is poured onto 200 g ice and extracted with 50 ml dichloromethane. The organic phase is dried on $Na_2SO_4$ and evaporated. The residue is vacuum distilled twice (9-10 mbar, 52-70° C.) in a Kugelrohr distillation apparatus. The isolated yield of the desired cyclohexene product is 60% (5.0 g).

Example 2

Lewis Acid Catalyzed Diels-Alder Cycloaddition

In this example, a substituted cyclohexene product comprising predominately cis-1-(2,6,6-trimethylcyclohex-3-en-1-yl)ethanone is formed. The $\alpha,\beta$-unsaturated carbonyl dienophile is mesityl oxide, the 1,3-diene is piperylene, and the Lewis acidic ionic liquid is $GaCl_3:[C_2mim]Cl$.

One equivalent of mesityl oxide (50 mmol; 5.7 mL) is added slowly with vigorous stirring at room temperature (16-19° C.) under nitrogen atmosphere to 2.15 equivalents (15.0 g) of freshly prepared $GaCl_3:[C_2mim]Cl$ (Lewis acid to ionic liquid ration=1.5:1.0). The mixture is stirred at room temperature for 1 hour. Five equivalents of piperylene (250 mmol; 25 mL) is added slowly to the reaction mixture at 0° C. with vigorous stirring and ice cooling over 40 min. The mixture is allowed to slowly warm to room temperature and stirred at room temperature for 6 days. The mixture is poured onto 200 g ice and extracted with 50 ml dichloromethane. The organic phase is dried on $Na_2SO_4$ and evaporated. The residue is vacuum distilled twice (9-10 mbar, 52-70° C.) in a Kugelrohr distillation apparatus. The isolated yield of the desired cyclohexene product is 24% (2.0 g).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Disclosure are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for producing substituted cyclohexenes comprising:

providing to a reactor an α,β-unsaturated carbonyl dienophile of Formula I

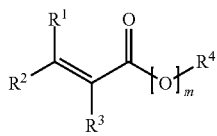

I wherein $R^1$, $R^2$, $R^3$ and $R^4$ are each independently selected from the group consisting of H and $C_1$-$C_4$ alkyl or $R^1$ and $R^2$, $R^1$ and $R^4$, $R^3$ and $R^4$, or $R^2$ and $R^3$ may optionally be joined together to form a 5-, 6-, or 7-membered ring, and m is 0 or 1;

providing to the reactor a 1,3-diene of Formula II

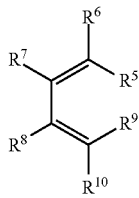

II wherein $R^5$, $R^6$, $R^7$, $R^8$, $R^9$ and $R^{10}$ are each independently selected from the group consisting of H and $C_1$-$C_4$ alkyl;

providing a Lewis acidic ionic liquid having a structure:

$$M(A)_n:[Cation]^+A^-,$$

wherein

M is a metal selected from the group consisting of Al, Ga, In, and Zr;

A is selected from the group consisting of Cl, Br, I, and $CF_3SO_3^-$;

n is an integer from 2 to 4; and

"Cation" is an ionic compound having a structure selected from the group consisting of:

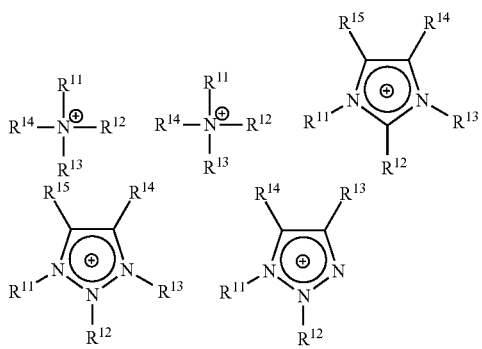

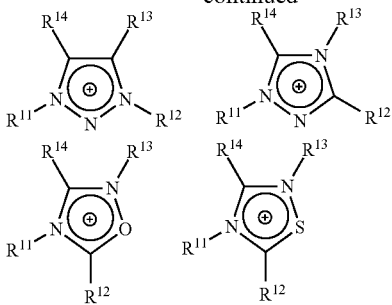

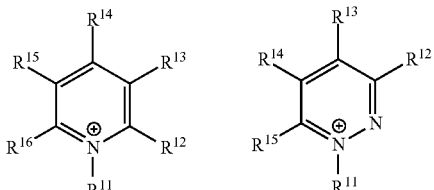

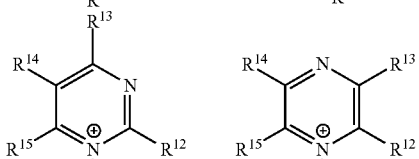

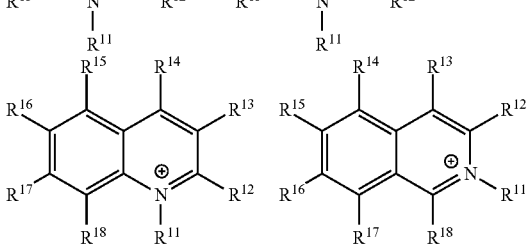

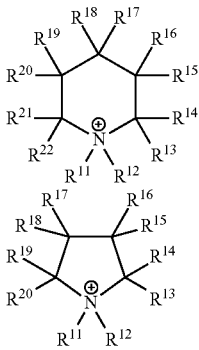

and where $R^{11}$ through $R^{22}$ are each independently a substituent selected from the group consisting of —H, —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, ($C_2$-$C_6$)alkenyl, hydroxyalkyl, haloalkyl, alkoxyalkyl, ($C_6$-$C_{10}$)aryl, and ($C_8$-$C_{16}$)alkenylaryl to the reactor; and reacting the α,β-unsaturated carbonyl dienophile with 1,3-diene to form a substituted cyclohexene product.

2. The process of claim 1, wherein the α,β-unsaturated carbonyl dienophile is selected from the group consisting of 3-methyl-2-butenal, 3-methyl-2-butenoic acid, methyl 3-methyl-2-butenoate, ethyl 3-methyl-2-butenoate, sec-butyl 3-methyl-2-butenoate, tert-butyl 3-methyl-2-butenoate, (E)-2-butenoic acid, methyl (E)-2-butenoate, ethyl (E)-2-butenoic acid, sec-butyl (E)-2-butenoic acid, tert-butyl (E)-2-butenoic acid, (E)-2-butenal, 3-butene-2-one, 3-methyl-3-pentene-2-one, 3-pentene-2-one, and mesityl oxide.

3. The process of claim 1, wherein the 1,3-diene is selected from the group consisting of piperylene, 2,4-hexadiene, 2-methyl-2,4-hexadiene, 4-methyl-1,3-pentadiene, isoprene, and butadiene.

4. The process of claim 3, wherein the Lewis acidic ionic liquid is selected from the group consisting of $AlCl_3$:[$C_n$mim]Cl; $GaCl_3$:[$C_n$mim]Cl; $ZrCl_4$:[$C_n$mim]Cl; $Al(OTf)_3$:[$C_n$mim][OTf]; and mixtures of any thereof, wherein n is an integer from 2 to 8.

5. The process of claim 3, wherein the Lewis acidic ionic liquid is selected from the group consisting of $AlCl_3$:[$C_2$mim]Cl; $AlCl_3$:[$C_8$mim]Cl; $GaCl_3$:[$C_2$mim]Cl; $ZrCl_4$:[$C_2$mim]Cl; $ZrCl_4$:[$C_8$mim]Cl; $Al(OTf)_3$:[$C_2$mim][OTf]; $Al(OTf)_3$:[$C_8$mim][OTf]; and mixtures of any thereof.

6. The process of claim 3, wherein the Lewis acidic ionic liquid has a Lewis acid to ionic liquid ratio ranging from 1:1 to 4:1.

7. The process of claim 1, wherein
the α,β-unsaturated carbonyl dienophile is mesityl oxide;
the 1,3-diene is piperylene; and
the Lewis acidic ionic liquid is $AlCl_3$:[$C_2$mim]Cl; $AlCl_3$:[$C_8$mim]Cl; or mixtures thereof.

8. The process of claim 7, wherein the substituted cyclohexene product comprises predominantly cis-1-(2,6,6-trimethylcyclohex-3-en-1-yl)ethanone.

9. The process of claim 8, further comprising:
converting the cis-1-(2,6,6-trimethylcyclohex-3-en-1-yl)ethanone to (±)-δ-damascone.

10. The process of claim 7, further comprising:
purifying the substituted cyclohexene product by one of distillation, vacuum distillation, fractional distillation, chromatography, crystallization and combinations of any thereof.

11. The process of claim 7, further comprising:
converting the substituted cyclohexene product to a fragrance product selected from the group consisting of (±)-(E)-α-damascone, (±)-(E)-β-damascone, (±)-(E)-δ-damascone, (±)-(E)-γ-damascone, 1-(2,2,6-trimethylcyclohexyl)-2-buten-1-one, 1-(2,2,6-trimethylcyclohexyl)-1-butanone, trans-4-(2,2,6-trimethylcyclohexyl)-3-buten-2-one, (±)-(E)-α-ionone, (±)-(E)-γ-ionone, (±)-dihydro-α-ionone, (±)-dihydro-γ-ionone, (±)-tetrahydroionone, methyl (±)-α-cyclogeranate, methyl (±)-β-cyclogeranate, ethyl (±)-β-cyclogeranate, ethyl (±)-β-safranate, methyl 2,2-dimethyl-6-methylenecyclohexane-1-carboxylate, ethyl 2,2-dimethyl-6-methylenecyclohexane-1-carboxylate, methyl 2,6,6-trimethyl-3-cyclohexene-1-carboxylate, ethyl 2,6,6-trimethylcyclohexane-1-carboxylate, 1-(2',2',6'-trimethylcyclohexyl)-3-pentanone, 1-(2',2',6'-trimethylcyclohexyl)-3-hexanone, 1-(2',2',6'-trimethylcyclohexyl)ethanone, (±)-dihydro-β-ionol, (±)-β-irone, (±)-γ-irone, (±)-α-irone, 2,4,6-trimethyl-3-cyclohexene-1-carbaldehyde,β-ionone, damascenone, γ-methyl ionone, β-methyl ionone, and any of these compounds wherein the C=O has been replaced with a CH—OH moiety.

12. The process of claim 7, further comprising:
converting the substituted cyclohexene product to (±)-γ-damascone.

13. A process for producing a substituted cyclohexene product comprising:
reacting mesityl oxide with piperylene in a Lewis acidic ionic liquid to form predominantly cis-1-(2,6,6-trimethylcyclohex-3-en-1-yl)ethanone, wherein the Lewis acidic ionic liquid is selected from the group consisting of $AlCl_3$:[$C_2$mim]Cl; $AlCl_3$:[$C_8$mim]Cl; $GaCl_3$:[$Cl_2$mim]Cl; $ZrCl_4$:[$C_2$mim]Cl; $ZrCl_4$:[$C_8$mim]Cl; $Al(OTf)_3$:[$C_2$mim][OTf]; $Al(OTf)_3$:[$E_8$mim][OTf]; and mixtures of any thereof.

14. The process of claim 13, wherein the Lewis acidic ionic liquid has a Lewis acid to ionic liquid ratio ranging from 1:1 to 4:1.

15. The process of claim 13, further comprising converting the cis-1-(2,6,6-trimethylcyclohex-3-en-1-yl)ethanone to (±)-δ-damascone.

16. The process of claim 13, further comprising:
epimerizing the cis-1-(2,6,6-trimethylcyclohex-3-en-1-yl)ethanone to trans-1-(2,6,6-trimethylcyclohex-3-en-1-yl)ethanone; and
condensing the trans-1-(2,6,6-trimethylcyclohex-3-en-1-yl)ethanone with an aldehyde to form a condensation product.

17. The process of claim 16, wherein the aldehyde is acetaldehyde and the condensation product is (±)-δ-damascone.

18. The process of claim 16, wherein the epimerizing step and the condensing step are performed in a single reactor.

19. The process of claim 16, further comprising purifying the condensation product by fractional distillation.

20. A process for producing (±)-δ-damascone comprising:
reacting mesityl oxide with piperylene in a Lewis acidic ionic liquid to form predominantly cis-1-(2,6,6-trimethylcyclohex-3-en-1-yl)ethanone;
epimerizing the cis-1-(2,6,6-trimethylcyclohex-3-en-1-yl)ethanone to trans-1-(2,6,6-trimethylcyclohex-3-en-1-yl)ethanone; and
condensing the trans-1-(2,6,6-trimethylcyclohex-3-en-1-yl)ethanone with acetaldehyde to form (±)-δ-damascone,
wherein the Lewis acidic ionic liquid is selected from the group consisting of $AlCl_3$:[$C_2$mim]Cl; $AlCl_3$:[$C_8$mim]Cl; and mixtures thereof.

21. The process of claim 20, wherein the epimerizing step and the condensing step are performed in a single reactor.

* * * * *